(12) United States Patent
Doan (10) Patent No.: US 6,687,550 B1
(45) Date of Patent: Feb. 3, 2004

(54) ACTIVE FIXATION ELECTRODE LEAD HAVING AN ELECTRICAL COUPLING MECHANISM

(75) Inventor: Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 365 days.

(21) Appl. No.: 09/872,550

(22) Filed: Jun. 1, 2001

(51) Int. Cl.[7] .................................................. A61N 1/05
(52) U.S. Cl. ..................................................... 607/127
(58) Field of Search ........................ 607/115–116, 119, 607/120, 122–123, 126–127; 600/372–375, 377, 381

(56) References Cited

U.S. PATENT DOCUMENTS

| 4,624,265 A | * | 11/1986 | Grassi | ........................ 607/123 |
| 5,447,533 A | | 9/1995 | Vachon et al. | .............. 607/120 |
| 5,716,390 A | * | 2/1998 | Li | .............................. 607/127 |

* cited by examiner

Primary Examiner—Kennedy Schaetzle
Assistant Examiner—Kristen Droesch (57) ABSTRACT

An implantable endocardial lead includes an electrical conductor coupled at its distal end to an active fixation electrode movable between a retracted position and an extended position advanced beyond the lead end for penetration into the myocardial tissue. A resilient coupling mechanism maintains electrical continuity between the active fixation electrode and an electrically active housing throughout movement of the electrode. In one instance, a conductive coupling is slidably received on a conductive shaft and is fixed to the electrically active housing. A compression spring is received on the conductive shaft intermediate and engaged with the conductive coupling and with a conductive ring stop member projecting radially from the conductive shaft. In another instance, an annular track member integral with the electrically active housing has an annular recess surrounding the conductive shaft and a metallic coil spring is received in the annular recess and slidably engageable with the conductive shaft.

21 Claims, 5 Drawing Sheets

ACTIVE FIXATION ELECTRODE LEAD HAVING AN ELECTRICAL COUPLING MECHANISM

FIELD OF THE INVENTION

The present invention relates generally to an implantable stimulation lead for use with an implantable pulse generator such as a cardiac pacemaker and, more specifically to such an implantable stimulation lead with the capability of anchoring an electrically active helix electrode at a desired site when the lead is fixated in the heart.

BACKGROUND OF THE INVENTION

Currently, known extendable/retractable screw-in implantable stimulation leads have an electrically active helix electrode. The helix electrode is directly connected to the distal coil conductor for the electrical connection and the extendable/retractable mechanism. In this design, the electrically active helix is intermittently in contact with the distal housing wherein the helix electrode resides. Therefore, in order to prevent chatter noises generated from the intermittent contacts between the helix and the distal housing, the distal housing must be of a nonconductive material such as plastic or ceramic. In this instance, since the distal tip is not electrically active during the lead implantation, in order to verify the pacing threshold and sensing amplitudes, the helix must be extended and fixated to the heart tissue. However, if the electrical measures are not acceptable, the helix must be retracted and again extended for fixation to a different implant site. This is considerably time consuming and inconvenient for the patient and for the implanter as well. To improve this situation, an electrically active mapping collar is incorporated onto the distal tip of the lead. This construction enables the implanter to choose an acceptable implant site before extending and fixating the helix to the final implant location. However, if the helix and housing collar are not continuously connected electrically, electrical noises or "chatter" would be generated from the intermittent contacts between the helix and distal housing and the lead would not be clinically acceptable. The chatter-free contact spring designs presented below will prevent the problem from occurring.

Typical of the known prior art is commonly assigned U.S. Pat. No. 5,447,533 to Vachon et al., which discloses a helix electrode system employed with an implantable stimulation lead.

It was in light of the foregoing that the present invention was conceived and has now been reduced to practice.

SUMMARY OF THE INVENTION

An implantable endocardial lead is disclosed for use with a cardiac stimulation device. The lead includes an electrical conductor whose proximal end is coupled to an electrical connector. An active fixation electrode is coupled to the distal end of the conductor, being movable between a retracted position fully within the lead and an extended position advanced beyond the distal end of the lead for effecting penetration into the myocardial tissue. A resilient coupling mechanism maintains electrical continuity between the active fixation electrode and the electrically active housing throughout movement of the active fixation electrode between the retracted position and the extended position. In one instance, a conductive coupling is slidably received on a conductive shaft and is fixed to the electrically active housing. A compression spring is received on the conductive shaft intermediate and engaged with the conductive coupling and with a conductive stopper including a ring member fixed to the conductive shaft and projecting radially from its longitudinal axis to a peripheral rim beyond the outer surface of the conductive shaft. In another instance, an annular track member integral and in electrical continuity with the electrically active housing has an annular recess surrounding the conductive shaft and a metallic coil spring received in the annular recess and slidably engageable with the conductive shaft.

Thus, in order to prevent the "electrical chatter" problem described above generated by two electrically conductive parts (a helix electrode and a conductive housing) in intermittent contact, in one embodiment a compression contact spring is used to provide a positive electrical connection between the two electrically active and moving parts. In an alternative design, a "ball seal" type contact spring can also be used for the same purpose.

Accordingly, a primary feature of the invention is to provide an implantable stimulation lead in which the electrically active helix electrode of an extendable/retractable design is continuously in contact with the distal housing in which the helix electrode resides.

Another feature of the present invention is to provide such an implantable stimulation lead which is of a "chatter-free" construction.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENTS

Figure 1:
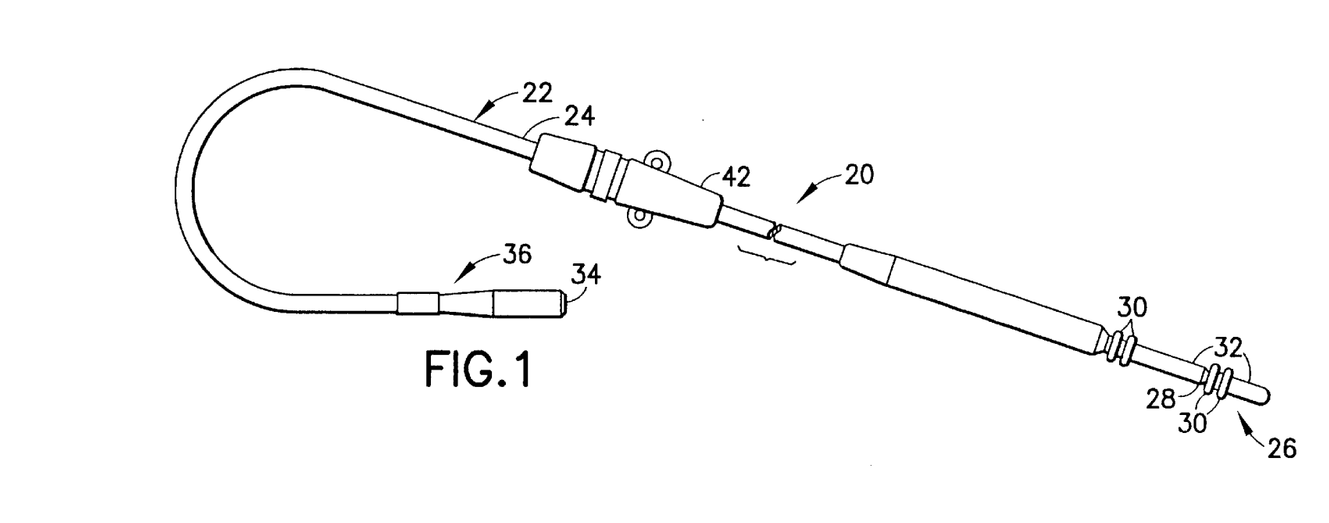
FIG. 1. is a side elevation view of a pacing lead of the type which can employ the present invention.

Turn now to the drawings and, initially to FIG. 1, which generally illustrates a perspective view of an implantable endocardial lead 20 intended for use with a cardiac stimulation device such as a pacemaker. Although the present invention will be described with reference to the embodiments shown in the drawings, it should be understood that the present invention can be embodied in many alternate forms or embodiments. In addition, any suitable size, shape or type of elements or materials may be used.

FIG. 1 illustrates a known pacing lead 20 designed for intravenous insertion and contact with the endocardium, and as such, may be conventionally referred to as an endocardial lead. The lead 20 is designed for intravenous insertion and contact with the endocardium and, as such, may be conventionally referred to as an endocardial lead. The lead 20 is provided with an elongated lead body 22, which includes coil or helically wound electrical conductors (not shown in this view) covered with an insulation sheath 24. The insulation sheath is preferably fabricated of silicone rubber, polyurethane or other suitable plastic. At a proximal end 26 of the pacing lead 20 is a connector assembly 28, which is provided with sealing rings 30, and which carries at least one, and preferably a pair of electrical contacts 32.

The connector assembly 28 is constructed using known techniques and is preferably fabricated of silicone rubber, polyurethane or other suitable plastic. Contacts 32 are preferably fabricated of stainless steel or other suitable electrically conductive material. The lead 20 is constructed to include a hollow interior extending from the proximal end 26 to a distal end 34. The hollow interior allows for the introduction of a stylet during implant, which is beneficial in allowing the surgeon to guide the otherwise flexible lead 20 from the point of venous insertion to the myocardium.

At the distal end 34 of the pacing lead 20 is an electrode assembly 36, which is discussed in more detail below. A suture sleeve 42, slidably mounted around lead body 22, serves to stabilize the pacing lead 20 at the site of venous insertion.

Figure 2:
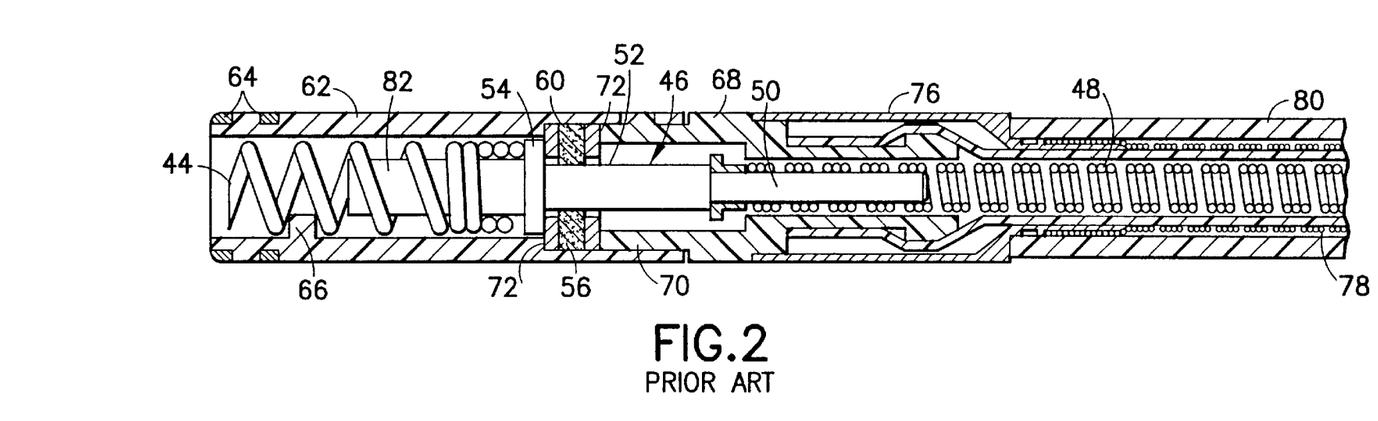
FIG. 2. is a longitudinal cross section view of a known electrode assembly at the distal end of the pacing lead illustrated in FIG. 1, with the helical electrode in the retracted position.
Figure 3:
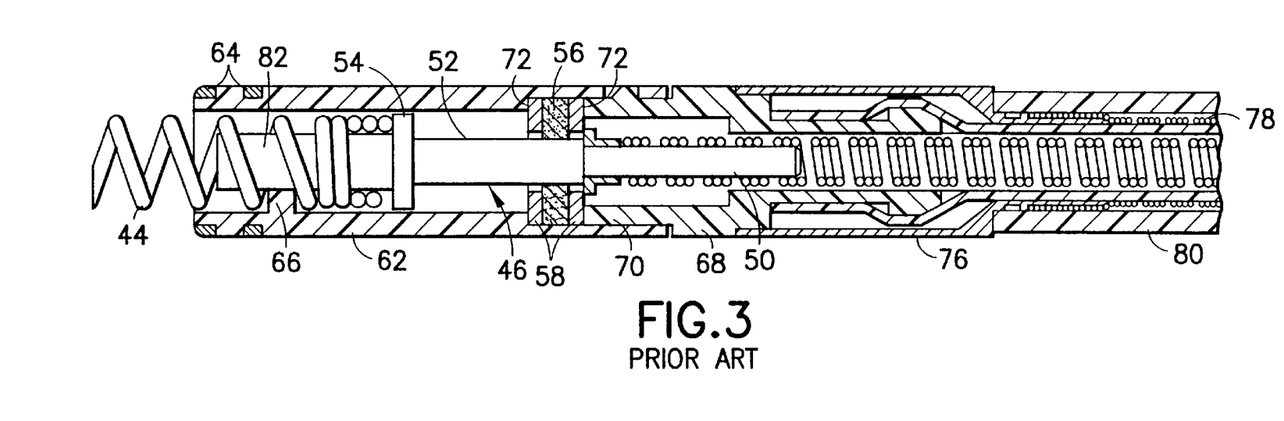
FIG. 3, is a longitudinal cross section view of the known electrode assembly at the distal end of the pacing lead illustrated in FIG. 1, with the helical electrode in the extended position.

FIGS. 2 and 3 depict a known construction for the distal end 36 of the pacing lead 20 of FIG. 1. In FIGS. 2 and 3, a helical electrode 44 is affixed to an advanceable electrical interconnect 46. The electrical interconnect 46 is also electrically connected to the conductor 48 which extends from the distal end to the proximal end of the pacing lead 20. The electrical interconnect 46 thus includes a tail portion 50, to which the conductor 48 is secured, a central shaft portion 52 and a head portion 54. The helical electrode 44 is connected to the head portion 54. The central shaft portion 52 of the electrical interconnect 46 passes through a seal assembly 56. The seal assembly 56 may include a pair of retaining rings 58 which cooperate to secure a resilient ring seal 60. The seal assembly 56 prevents bodily fluids from penetrating into the axial void extending through the center of the pacing lead 20.

As also depicted in FIGS. 2 and 3, the distal end 34 of the pacing lead 20 terminates in a sleeve 62 which is essentially a cylindrical element having a central bore within which the helical electrode 44 is disposed and retractable. The sleeve 62 is preferably fabricated from a biocompatible elastomeric material. The distal tip of sleeve 62 may include one or more metallic rings 64, which are useful during implant to allow a physician to verify the position of the helical electrode 44 relative to the metallic ring 64 in either the extended or retracted position by the use of a fluoroscope. Further, the sleeve 62 includes a knob 66 extending from the inner diameter to guide the rotative advancement of the helical electrode 44. It is to be understood that techniques for implanting a pacing lead and advancing the fixation elements are known in the art, and, therefore, will not be discussed here.

The proximal end of the sleeve 62 is affixed to a stepped cylindrical element 68, which is preferably formed from a biocompatible nonconductive material. The stepped cylindrical element 68 includes a cylindrical portion 70 which slides into the proximal end of the cylindrical sleeve 62 and is bonded thereto. The seal assembly 56 is located between an end-face 72 of the stepped cylindrical element 68 and an internal step 74 of the sleeve 62.

As further illustrated in FIGS. 2 and 3, the proximal end of the distal assembly 36 may include a second ring electrode or sensor electrode 76 spaced proximally of the distal tip. The ring electrode 76 is electrically interconnected to a second conductor 78 which also extends from the proximal to the distal end of the lead body 22 and is helically wrapped about the cylindrical insulation containing the first conductor 48. The second electrical conductor 78 is also preferably encased in an insulation sleeve 80. The second electrical conductor 78 extends to and interconnects with an electrical contact (not shown) located at the connector assembly 28 at the proximal end 26 of the pacing lead 20.

In FIGS. 2 and 3, a therapeutic delivery means is provided which includes a therapeutic bullet 82 centrally disposed with respect to the helical electrode 44, that is, along the axis of the helix. The therapeutic bullet 82 is preferably secured to the head portion 54 of the electrical interconnect 46, and advanceable therewith. As depicted in FIG. 3, when the helical electrode 44 is fully extended and inserted into the myocardium upon implant, the therapeutic bullet 82 does not extend out of the end of the sleeve 62 as does the helical electrode 44. Although, according to the design illustrated in FIGS. 2 and 3, the therapeutic bullet 82 is only advanceable with the advancement of the electrical interconnect 46, other constructions are known according to which the therapeutic bullet is independently advanceable.

With the construction just described, it was earlier explained that since the distal tip is not electrically active during the lead implantation, in order to verify the pacing threshold and sensing amplitudes, the helical electrode 44 must be extended and fixated to the heart tissue. However, if the electrical measures are not acceptable, the helix must be retracted and again extended for fixation to a different implant site. This is considerably time consuming and inconvenient for the patient and for the implanter as well.

Figure 4:
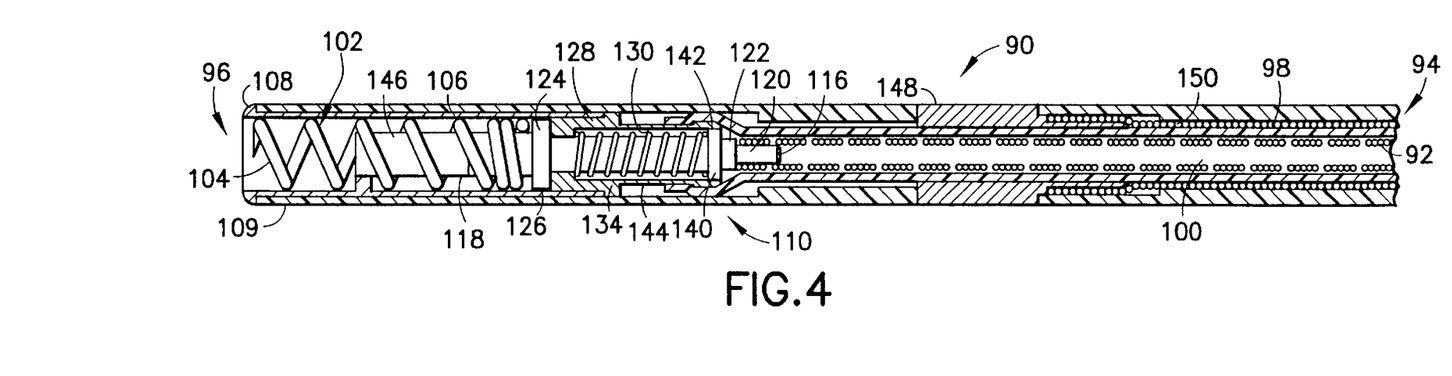
FIG. 4. is a longitudinal cross section view, similar to FIG. 2, of an electrode assembly embodying the present invention and located at the distal end of the pacing lead illustrated in FIG. 1, with the helical electrode in the retracted position.
Figure 5:
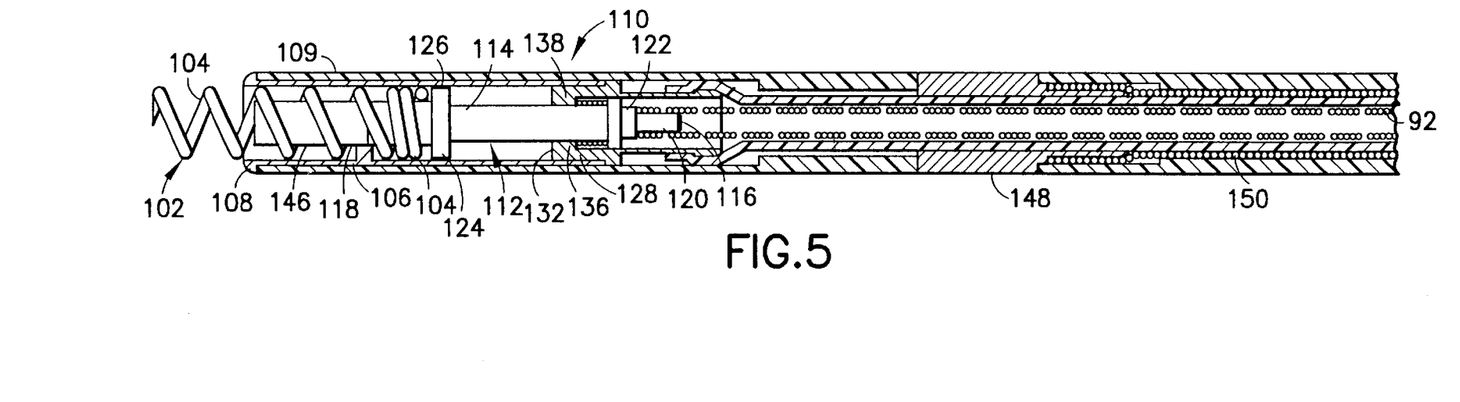
FIG. 5. is a longitudinal cross section view, similar to FIG. 3, of an electrode assembly embodying the present invention and located at the distal end of the pacing lead illustrated in FIG. 1, with the helical electrode in the extended position.

It was to avoid this situation that the present invention was sought. Turning now to FIGS. 4 and 5, with continued reference to FIG. 1, an implantable endocardial lead 90 is illustrated which extends between proximal and distal ends (as with the lead 20) for use with a cardiac stimulation device such as a pacemaker. In this instance, an electrical conductor 92 within the lead 90 extends between proximal and distal ends generally indicated by reference numerals 94, 96, respectively. An insulation sheath 98 covers the conductor 92 and, together, the insulation sheath and the conductor define an internal chamber 100 which extends from the proximal end to the distal end of the lead 90. As in the instance of the lead 20, the lead 90 also has one or more electrical contacts 32 coupled to the proximal end of the electrical conductor 92.

In a manner to be described in more detail below, an active fixation electrode 102 is coupled to the distal end of the conductor 92. The active fixation electrode includes an electrically active helix 104 which is movable between a retracted position (FIG. 4) fully within the lead and an extended position (FIG. 5) advanced beyond the distal end of the lead for effecting penetration into the myocardial tissue. Further, the lead 90 includes an electrically active housing 106 at its distal end, terminating at an integral electrically active collar 108 which is coaxial with the helix 104 at the distal end of the lead. A sleeve 109 of silicone rubber or other suitable dielectric material overlies the electrically active housing while leaving exposed the collar 108. A resilient coupling mechanism 110 is provided for maintaining electrical continuity between the active fixation electrode and the electrically active housing throughout movement of the active fixation electrode between the retracted position and the extended position. This component, also, will be described in greater detail below.

A conductive shaft 112 positioned within the internal chamber 100 has a longitudinal axis generally coaxial with the electrical conductor 92. The conductive shaft 112 has an outer surface 114 and extends between proximal and distal ends 116, 118, respectively. The electrical conductor 92 is fixed to the proximal end of the conductive shaft 112 as by being crimped onto a tail portion 120, then welded to an annular shoulder 122. An annular collar 124 is integral with the conductive shaft 112 at a location intermediate the proximal and distal ends 116, 118 and projects radially from the longitudinal axis of the conductive shaft to an outer rim 126 which lies beyond the outer surface 114 of the conductive shaft.

Figure 4A:
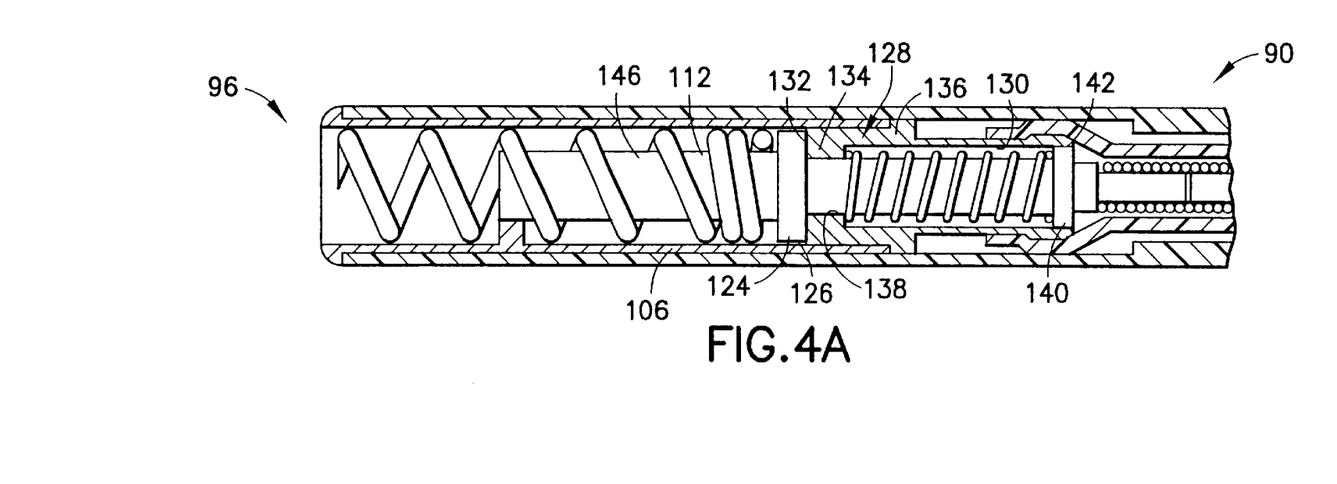
FIG. 4A is a longitudinal cross section view, an enlarged detail view of portions illustrated in FIG. 4.

The resilient coupling mechanism 110 includes a tubular conductive coupling 128 suitably fixed to the electrically active housing 106 and coaxial with and slidably received on the conductive shaft 112. The tubular conductive coupling 128 has an internal peripheral surface 130, or annular track member, facing and spaced from a part of the conductive shaft 112 and has a distal terminal surface 132. In actual fact, the conductive coupling 128 is cup-shaped including a base 134 lying in a plane transverse of the longitudinal axis of the conductive shaft 112 and a cylindrical sidewall 136 upstanding from the base and coaxial with the longitudinal axis of the conductive shaft. The base 134 has a bore 138 for slidable reception on the conductive shaft 112. A conductive stopper 140, adjacent the annular shoulder 122, is integral with the conductive shaft and includes a ring member projecting radially from the longitudinal axis to a peripheral rim 142 beyond the outer surface of the conductive shaft. A compression spring 144 is positioned intermediate and engaged with the base 134 of the conductive coupling 128 and with the conductive stopper 140.

The annular collar 124 is engaged with the distal terminal surface 132 of the conductive coupling 128 when the active fixation electrode 102 is in the retracted position (FIG. 4) and is spaced from the distal terminal surface of the conductive coupling when the active fixation electrode is in the extended position (FIG. 5). Throughout movement of the shaft 112 between the retracted and extended positions, electrical continuity is maintained between the active fixation electrode 102 and the electrically active housing 106 with the assistance of the compression spring 144. With this construction, the chatter noises, which often occurred with prior designs, is avoided.

The lead 90 may also include a therapeutic element or steroid plug 146 generally cylindrical in shape coaxial with and integral with the active fixation electrode 102 formed of a biocompatible matrix material. The therapeutic element 146 may be of a known design and composition and will not now be further described.

It will also be appreciated that the lead 90 may be of bipolar construction including a ring electrode 148 spaced from the distal end 96 of the lead, a second electrical conductor 150 within the lead extending between proximal and distal ends, and a second electrical contact (not shown) coupled to the proximal end of the second electrical conductor.

Figure 6:
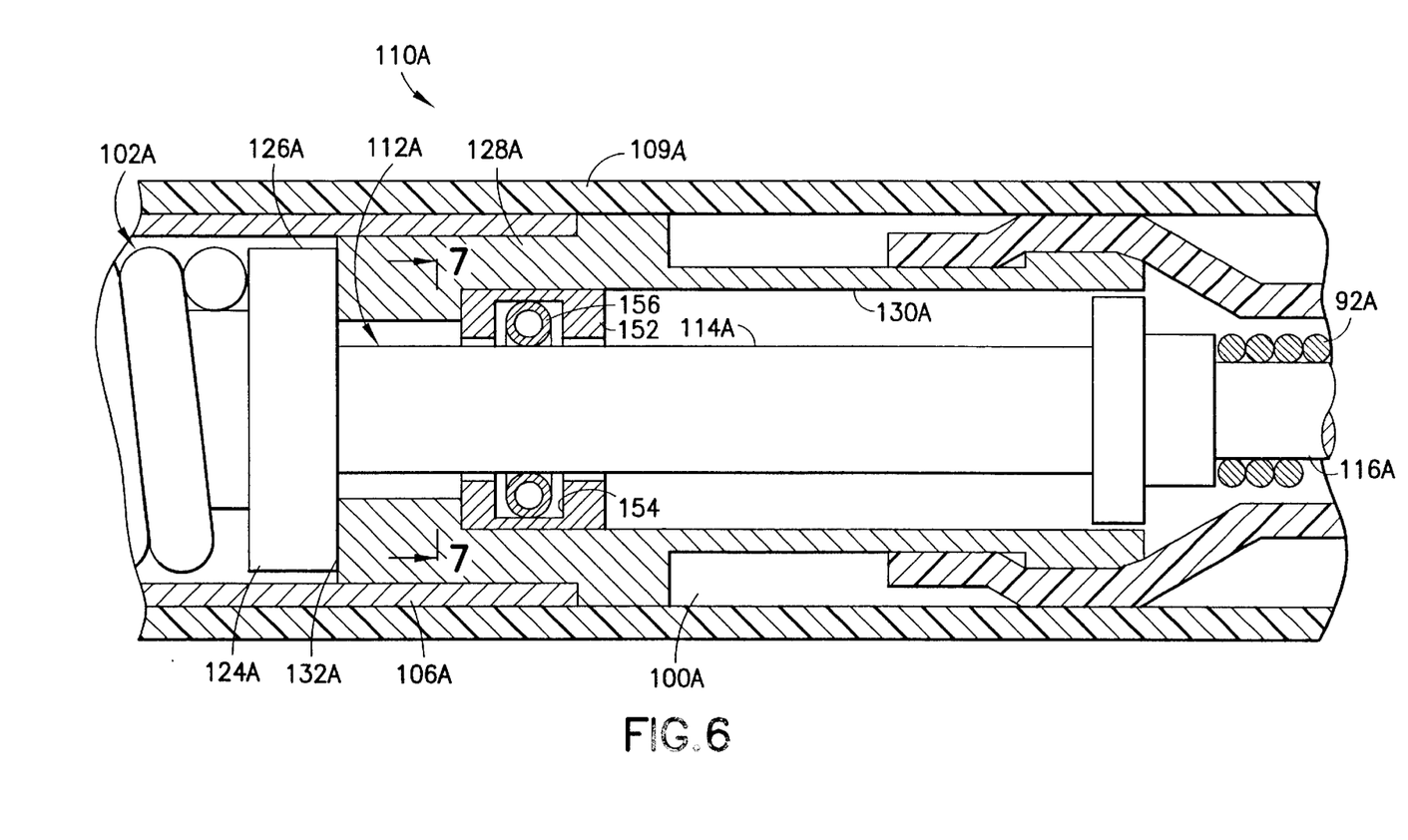
FIG. 6 is a detail cross section view generally illustrating a portion of the electrode assembly depicted in FIGS. 4 and 5, but depicting another embodiment of the invention.
Figure 7:
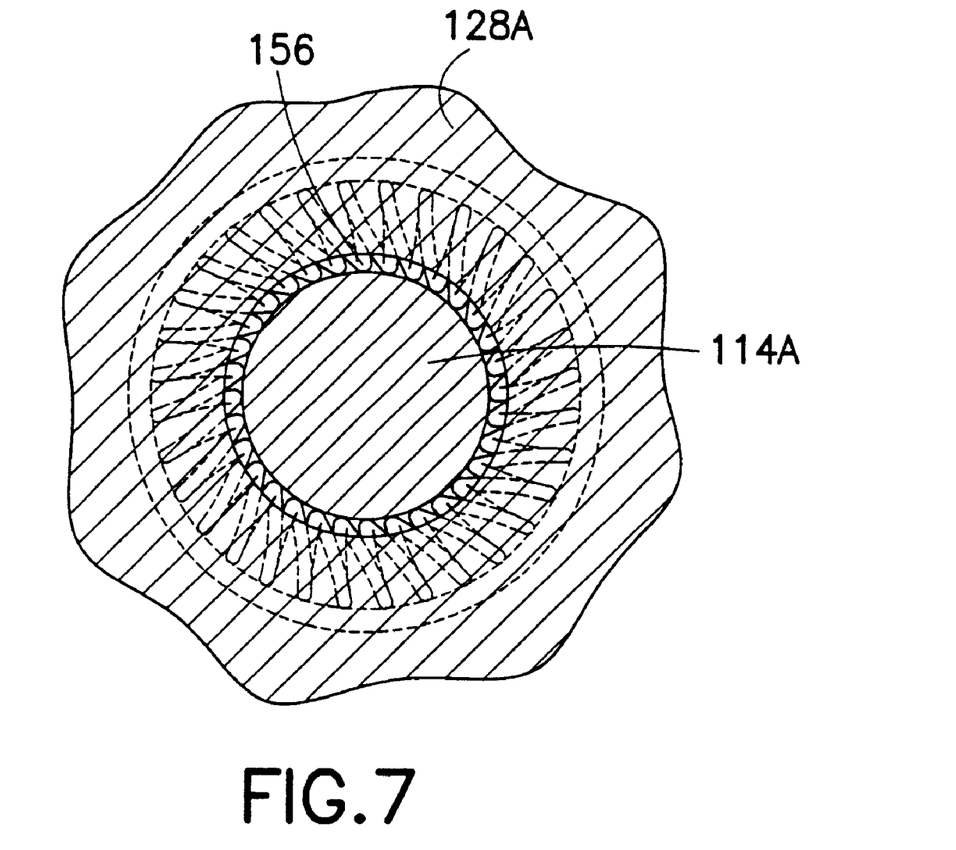
FIG. 7 is a detailed cross-section view taken generally along line 7—7 in FIG. 6.

Turn now to FIGS. 6 and 7 for the description of another embodiment of the invention. In this instance, a conductive shaft 112A has a longitudinal axis aligned with that of the internal chamber 100A generally coaxial with the electrical conductor 92A. The conductive shaft 112A has an outer surface 114A and extends between proximal and distal ends in the manner of the conductive shaft 112. The electrical conductor 92A is suitably fixed to the proximal end 116A of the conductive shaft 112A. An annular collar 124A is integral with the conductive shaft 112A intermediate its proximal and distal ends and projects radially from the longitudinal axis of the conductive shaft to an outer rim 126A beyond the outer surface 114A of the conductive shaft.

As with the embodiment of FIGS. 4 and 5 which includes a resilient coupling mechanism 110 for maintaining electrical continuity between the active fixation electrode 102 and the electrically active housing 106, the embodiment of FIG. 6 includes a modified resilient coupling mechanism 11A. Also, as with the embodiment of FIGS. 4 and 5, a sleeve 109A of silicone rubber or other suitable dielectric material overlies the electrically active housing. A tubular conductive coupling 128A is suitably fixed to the electrically active housing 106A and coaxial with the conductive shaft 112A and has an internal peripheral surface 130A facing and spaced from the outer surface 114A of the conductive shaft and has a distal terminal surface 132A. An annular track member 152 is fixed to the internal peripheral surface 130A of the tubular conductive coupling 128A and has an annular recess 154 surrounding the conductive shaft 112A. A metallic coil spring 156 is received in the annular recess 154 and is slidably engageable with the outer surface 114A of the conductive shaft. The coil spring 156 is in the nature of a garter spring, that is, an elongated helical spring manipulated into toroidal shape. The annular collar 124A is engaged with the distal terminal surface 132A of the tubular conductive coupling 128A when the active fixation electrode 102A is in the retracted position (generally as seen in FIG. 4) and is spaced from the distal terminal surface of the tubular conductive coupling when the active fixation electrode is in the extended position (generally as seen in FIG. 5). Throughout movement of the shaft 112A between the retracted and extended positions, electrical continuity is maintained between the active fixation electrode 102A and the electrically active housing 106A with the assistance of the compression spring 144 thereby avoiding the chatter noises which often occurred with prior designs.

It should be understood that the foregoing description is only illustrative of a pair of embodiments of the invention. Various alternatives and modifications can be devised by those skilled in the art without departing from the invention. Accordingly, the present invention is intended to embrace all such alternatives, modifications and variances, which fall within the scope of the appended claims.

What is claimed is:

1. An implantable endocardial lead extending between proximal and distal ends for use with a cardiac stimulation device comprising:

an electrical conductor within the lead extending between proximal and distal ends;

an insulation sheath covering the conductor;

an electrical connector coupled to the proximal end of the conductor;

an active fixation electrode coupled to the distal end of the conductor and movable between a retracted position and an extended position advanced beyond the distal end of the lead for effecting penetration into the myocardial tissue;

an electrically active housing at the distal end of the lead;

a resilient coupling mechanism for maintaining electrical continuity between the active fixation electrode and the electrically active housing throughout movement of the active fixation electrode between the retracted position and the extended position and a conductive shaft having a longitudinal axis that is generally coaxial with the electrical conductor, the conductive shaft having an outer surface and extending between proximal and distal ends, the electrical conductor being fixed to the proximal end thereof; and wherein the resilient coupling mechanism includes:
a conductive coupling slidably received on the conductive shaft and fixed to the electrically active housing;
a conductive stopper fixed to the conductive shaft including a ring member projecting radially from the longitudinal axis to a peripheral rim beyond the outer surface of the conductive shaft; and
a compression spring intermediate and engaged with the conductive coupling and with the conductive stopper.

2. The implantable endocardial lead as set forth in claim 1:
wherein the active fixation electrode includes an electrically active helix advanceable outward relative to the distal end of the conductor for effecting penetration into myocardial tissue.

3. The implantable endocardial lead as set forth in claim 1 including:
a therapeutic element integral with the active fixation electrode formed of a biocompatible matrix material.

4. The implantable endocardial lead as set forth in claim 1 including:
a therapeutic element generally cylindrical in shape coaxial with and fixed on the distal end of the conductive shaft and formed of a biocompatible matrix material.

5. The implantable endocardial lead as set forth in claim 1:
wherein the conductive coupling is cup-shaped including a base lying in a plane transverse of the longitudinal axis of the conductive shaft and a cylindrical sidewall upstanding from the base and coaxial with the longitudinal axis of the conductive shaft, the base having a bore for slidable reception on the conductive shaft; and
wherein the compression spring extends between the base and the conductive stopper.

6. The implantable endocardial lead as set forth in claim 5:
wherein the sidewall and base of the conductive coupling define a cavity for reception of the conductive shaft, the conductive stopper, and the compression spring coaxially received on the conductive shaft.

7. The implantable endocardial lead as set forth in claim 1:
wherein the active fixation electrode includes an electrically active helix advanceable outward relative to the distal end of the conductor for effecting penetration into myocardial tissue; and
wherein the electrically active housing includes an electrically active collar coaxial with the helix at the distal end of the lead.

8. The implantable endocardial lead as set forth in claim 1:
wherein the lead is of bipolar construction; and including:
a ring electrode spaced from the distal end of the lead;
a second electrical conductor within the lead extending between proximal and distal ends; and
a second electrical contact coupled to the proximal end of the second electrical conductor.

9. An implantable endocardial lead extending between proximal and distal ends for use with a cardiac stimulation device comprising:
an electrical conductor within the lead extending between proximal and distal ends;
an insulation sheath covering the conductor;
an electrical connector coupled to the proximal end of the conductor;
an active fixation electrode coupled to the distal end of the conductor and movable between a retracted position and an extended position advanced beyond the distal end of the lead for effecting penetration into the myocardial tissue;
an electrically active housing at the distal end of the lead;
a resilient coupling mechanism for maintaining electrical continuity between the active fixation electrode and the electrically active housing throughout movement of the active fixation electrode between the retracted position and the extended position;
a conductive shaft having a longitudinal axis that is generally coaxial with the electrical conductor, the conductive shaft having an outer surface and extending between proximal and distal ends, the electrical conductor being fixed to the proximal end thereof; and
an annular collar integral with the conductive shaft intermediate the proximal and distal ends and projecting radially from the longitudinal axis to an outer rim beyond the outer surface of the conductive shaft; and wherein the resilient coupling mechanism includes:
a tubular conductive coupling fixed to the electrically active housing and coaxial with and slidably received on the conductive shaft and having an internal peripheral surface facing and spaced from a part of the conductive shaft and having a distal terminal surface;
a conductive stopper integral with the conductive shaft including a ring member projecting radially from the longitudinal axis to a peripheral rim beyond the outer surface of the conductive shaft; and
a compression spring intermediate and engaged with the conductive coupling and with the conductive stopper;
the annular collar being engaged with the distal terminal surface of the conductive coupling when the active fixation electrode is in the retracted position and being spaced from the distal terminal surface of the conductive coupling when the active fixation electrode is in the extended position.

10. The implantable endocardial lead as set forth in claim 9:
wherein the active fixation electrode includes an electrically active helix advanceable outward relative to the distal end of the conductor for effecting penetration into myocardial tissue.

11. The implantable endocardial lead as set forth in claim 9 including:
a therapeutic element integral with the active fixation electrode formed of a biocompatible matrix material.

12. The implantable endocardial lead as set forth in claim 9 including:
a therapeutic element generally cylindrical in shape coaxial with and fixed on the distal end of the conductive shaft and formed of a biocompatible matrix material.

13. The implantable endocardial lead as set forth in claim 9:
wherein the active fixation electrode includes an electrically active helix advanceable outward relative to the distal end of the conductor for effecting penetration into myocardial tissue; and
wherein the electrically active housing includes an electrically active collar coaxial with the helix at the distal end of the lead.

14. The implantable endocardial lead as set forth in claim 9:
   wherein the lead is of bipolar construction; and including:
       a ring electrode spaced from the distal end of the lead;
       a second electrical conductor within the lead extending between proximal and distal ends; and
       a second electrical contact coupled to the proximal end of the second electrical conductor.

15. An implantable endocardial lead extending between proximal and distal ends for use with a cardiac stimulation device comprising:
   an electrical conductor within the lead extending between proximal and distal ends;
   an insulation sheath covering the conductor;
   an electrical connector coupled to the proximal end of the conductor;
   an active fixation electrode coupled to the distal end of the conductor and movable between a retracted position and an extended position advanced beyond the distal end of the lead for effecting penetration into the myocardial tissue;
   an electrically active housing at the distal end of the lead;
   a resilient coupling mechanism for maintaining electrical continuity between the active fixation electrode and the electrically active housing throughout movement of the active fixation electrode between the retracted position and the extended position; and
   a conductive shaft having a longitudinal axis that is generally coaxial with the electrical conductor, the conductive shaft having an outer surface and extending between proximal and distal ends, the electrical conductor being fixed to the proximal end thereof; and
   wherein the resilient coupling mechanism includes:
       an annular track member integral and in electrical continuity with the electrically active housing and having an annular recess surrounding the conductive shaft; and
       a metallic coil spring received in the annular recess and slidably engageable with the conductive shaft.

16. The implantable endocardial lead as set forth in claim 15:
   wherein the annular track member is coaxial with the conductive shaft.

17. The implantable endocardial lead as set forth in claim 15:
   wherein the active fixation electrode includes an electrically active helix advanceable outward relative to the distal end of the conductor for effecting penetration into myocardial tissue.

18. The implantable endocardial lead as set forth in claim 15 including:
   a therapeutic element integral with the active fixation electrode formed of a biocompatible matrix material.

19. The implantable endocardial lead as set forth in claim 15 including:
   a therapeutic element generally cylindrical in shape coaxial with and fixed on the distal end of the conductive shaft and formed of a biocompatible matrix material.

20. The implantable endocardial lead as set forth in claim 15:
   wherein the active fixation electrode includes an electrically active helix advanceable outward relative to the distal end of the conductor for effecting penetration into myocardial tissue; and
   wherein the electrically active housing includes an electrically active collar coaxial with the helix at the distal end of the lead.

21. An implantable endocardial lead extending between proximal and distal ends for use with a cardiac stimulation device comprising:
   an electrical conductor within the lead extending between proximal and distal ends;
   an insulation sheath covering the conductor;
   an electrical connector coupled to the proximal end of the conductor;
   an active fixation electrode coupled to the distal end of the conductor and movable between a retracted position and an extended position advanced beyond the distal end of the lead for effecting penetration into the myocardial tissue;
   an electrically active housing at the distal end of the lead;
   a resilient coupling mechanism for maintaining electrical continuity between the active fixation electrode and the electrically active housing throughout movement of the active fixation electrode between the retracted position and the extended position;
   a conductive shaft having a longitudinal axis that is generally coaxial with the electrical conductor, the conductive shaft having an outer surface and extending between proximal and distal ends, the electrical conductor being fixed to the proximal end thereof; and
   an annular collar integral with the conductive shaft intermediate the proximal and distal ends and projecting radially from the longitudinal axis to an outer rim beyond the outer surface of the conductive shaft; and
   wherein the resilient coupling mechanism includes:
       a tubular conductive coupling fixed to the electrically active housing and coaxial with the conductive shaft and having an internal peripheral surface facing and spaced from a part of the conductive shaft and having a distal terminal surface;
       an annular track member fixed to the tubular conductive coupling and having an annular recess surrounding the conductive shaft; and
       a metallic coil spring received in the annular recess and slidably engageable with the conductive shaft;
       the annular collar being engaged with the distal terminal surface of the conductive coupling when the active fixation electrode is in the retracted position and being spaced from the distal terminal surface of the conductive coupling when the active fixation electrode is in the extended position.

* * * * *